(12) United States Patent
Hayden et al.

(10) Patent No.: US 6,206,702 B1
(45) Date of Patent: Mar. 27, 2001

(54) METHODS AND DEVICES FOR TREATING UNILATERAL NEGLECT

(76) Inventors: Deborah A. Hayden, 402 Connie Dr., Jackson, MO (US) 63755; William T. Cranford, 21520 Port Hickey Rd., Zachary, LA (US) 70791

( * ) Notice: Subject to any disclaimer, the term of this patent is extended or adjusted under 35 U.S.C. 154(b) by 0 days.

(21) Appl. No.: 09/379,971

(22) Filed: Aug. 24, 1999

(51) Int. Cl.[7] .................................................. H04M 11/00
(52) U.S. Cl. ............................................................ 434/236
(58) Field of Search ................................... 600/558, 300; 128/905, 920; 434/236, 327; 351/203, 209

(56) References Cited

U.S. PATENT DOCUMENTS

| | | |
|---|---|---|
| 5,052,401 | 10/1991 | Sherwin . |
| 5,163,690 | 11/1992 | Davis et al. . |
| 5,241,332 * | 8/1993 | Farrell .................................. 351/203 |
| 5,260,869 | 11/1993 | Ferrier et al. . |
| 5,520,543 | 5/1996 | Mitui . |
| 5,678,571 | 10/1997 | Brown . |
| 5,692,517 | 12/1997 | Junker . |
| 5,711,671 | 1/1998 | Geeslin et al. . |
| 5,713,794 | 2/1998 | Shimojima et al. . |
| 5,725,472 | 3/1998 | Weathers . |
| 5,828,943 | 10/1998 | Brown . |

* cited by examiner

*Primary Examiner*—William E. Kamm
(74) *Attorney, Agent, or Firm*—Howell & Haferkamp, LC

(57) ABSTRACT

Unilateral neglect is treated using a computer-controlled therapy system and method, and a stored computer program. A patient requiring therapy is placed in front of a computer controlled display. Stimuli are displayed on the screen to the patient, and responses to the stimuli on the side of the patient subject to neglect are solicited. The stimuli may be presented in the form of an age-appropriate activity or game. The responses are quantitatively evaluated and the difficulty of the activity or game is adjusted in accordance with the evaluation. Various audio and video distractions may be provided to adjust the level of difficulty, and the evaluations may include measurement of the number of correct stimulus responses within a predetermined period of time, the length of time a patient neglects a stimulus appearing on that patient's neglected side, or both. The difficulty may be adjusted by adjusting various properties of the interactive stimuli, such as brightness, geometric complexity, visual contrast, speed of movement, and apparent dimensionality.

22 Claims, 3 Drawing Sheets

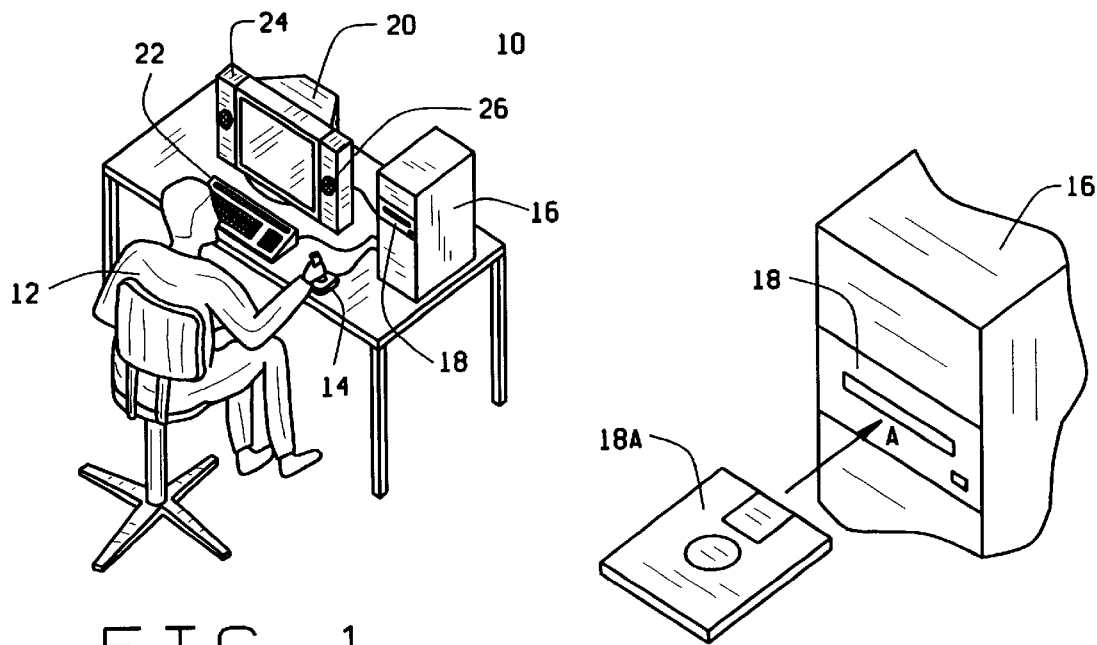
FIG. 1
FIG. 1A
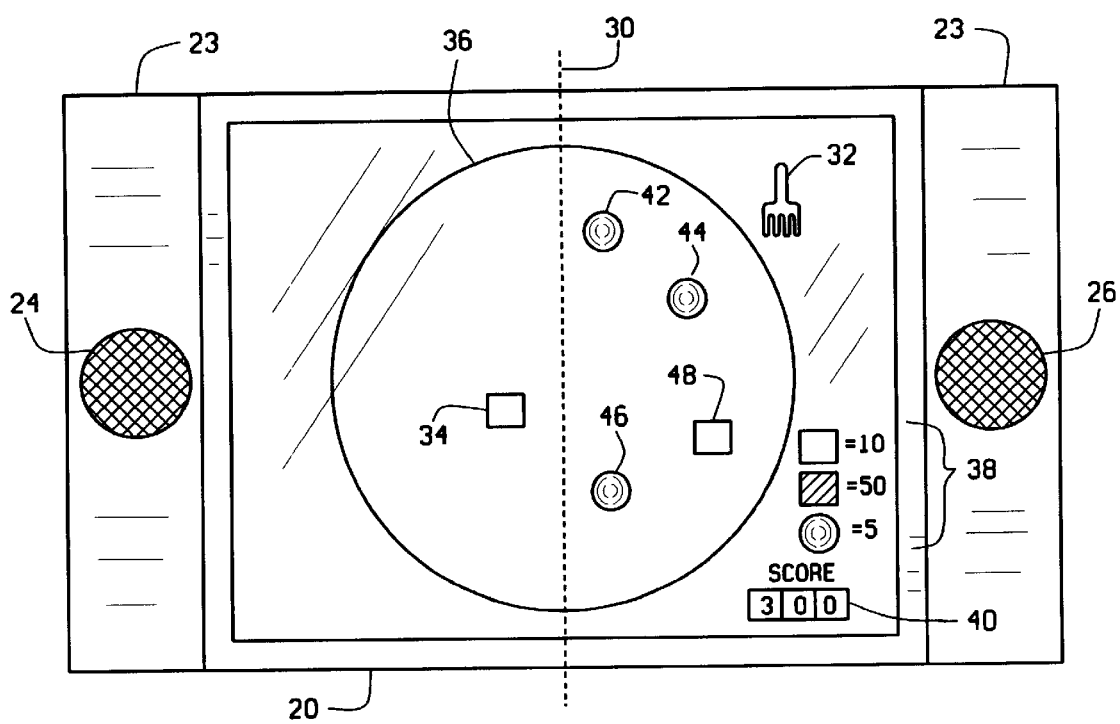
FIG. 2

METHODS AND DEVICES FOR TREATING UNILATERAL NEGLECT

BACKGROUND OF THE INVENTION

This invention relates to methods and devices for providing therapy to treat certain symptoms of brain lesions, and more particularly to methods and devices for treating unilateral neglect, a disorder manifested by a failure to respond or orient to stimuli presented contralateral to a brain lesion.

Unilateral neglect can have a global impact on the functioning of an individual, affecting work, play, leisure and self-care. A brain lesion that results in unilateral neglect may occur on either side of the brain, affecting a patient's responses to the opposite field of view. For example, a lesion on the right side of a person's brain may cause a failure to recognize the left side of a person's body and objects positioned to the left side of the person within the environment. Functional ability may be affected, in that such a person may also eat food only from the right side of a plate and comb his hair and brush his teeth only on the right side. Objects to the left side of the affected person may be ignored to such an extent that he walks into and collides with them, and the afflicted person may also appear to be inattentive to people entering the room at his left. Completion of a task that requires exploration of the left side of his field of view would prove to be quite difficult. Of course, if the lesion is on the left side of the affected person's brain, objects to the right of the person, rather than to the left, would be subject to neglect. This type of neglect is not itself caused by a defect in a patient's field of view, but rather is independent of any such defects.

Computer-aided treatment of human medical conditions is not, in itself, new. For example, a method for treating certain specific medical conditions using a microprocessor-based video game is described in Brown, U.S. Pat. No. 5,678,571. Brown discloses a method of treating a medical condition in a human patient, including the steps of choosing a psychological strategy for treating the medical condition, encoding electronic instructions for an interactive video game in such a way that the interactive video game implements the psychological strategy, loading the electronic instructions into a microprocessor-based unit equipped with a display for displaying the interactive video game and with a patient input device for receiving responses to the interactive video game from the human patient. The video game can also contain instructions for a scoring procedure to quantitatively analyze the medical condition of the human patient. However, the '571 patent is specifically directed at certain disorders and conditions, such as smoking, growth disorder, diabetes, asthma, eating disorder, and depression, rather than right or left side visual neglect.

U.S. Pat. No. 5,828,943, also to Brown, discloses a medical use for video games. However, the disclosure of this patent is directed specifically to an apparatus and methods for the diagnostic assessment of psychological conditions and not to their treatment. In addition, no treatment of visual neglect is shown or contemplated.

U.S. Pat. No. 5,711,671 to Geeslin et al. is directed to the use of an automated cognitive rehabilitation system and method for treating brain injured patients. It also discloses the use of a computer network to remotely treat a plurality of patients, to modify levels of difficulty, and to compile results. However, it does not disclose a method for treating visual neglect in a brain injury patient.

SUMMARY OF THE INVENTION

In order to solve these and other needs in the art, the inventors have succeeded at developing methods of, and devices for treatment of visual neglect manifested by a failure to respond or orient to stimuli presented contralateral to a brain lesion. The invention employs a computer software program that promotes awareness of the neglected side of an affected patient, visual scanning, and cognitive compensation, in addition to facilitating activation of the affected hemisphere of the brain. By addressing these areas, the resulting outcome is an overall improvement in functional performance.

There is thus provided, in accordance with a first aspect of the invention, a method for providing therapy for a person afflicted with unilateral neglect, the method comprising: (a) providing a computer-controlled display screen in front of the person, (b) displaying, on the display screen and under computer control, interactive stimuli to the person including stimuli on a side of the display screen that is subject to the person's neglect; (c) soliciting responses from the person including responses to the stimuli on the side subject to neglect; and (d) quantitatively evaluating the responses of the person to the solicited responses relating to the stimuli on the side subject to neglect to obtain a performance evaluation, the evaluation being indicative of a level of success of the person in overcoming visual neglect. The level of difficulty presented by the stimuli may be varied in accordance with the performance evaluation to exercise the person's responses to stimuli on the side subject to neglect. Sounds having directional properties may be added to enhance the effect of the therapy, and audio or visual distractions, or both, may be used to further exercise the person's responses.

In accordance with another aspect of the invention, there is provided a device for providing therapy for a person afflicted with unilateral neglect. The inventive device comprises (a) a display screen configured for placement in front of the person, (b) a computer including a stored program, the computer being coupled to the display screen to operatively display interactive stimuli including stimuli on a selected side of a vertical midline of the display screen; and (c) an input device operatively coupled to the computer and configured to receive responses from a person including responses evoked by the stimuli on the selected side of the display screen; the computer being configured so that the stored program controls the computer to present the stimuli and to quantitatively evaluate responses received from the input device, the evaluations being indicative of a level of success of a person in overcoming visual neglect. The device may also comprise a sound source that provides sounds that appear to emanate from different, selectable directions which may be coordinated with the stimuli on the screen. The stored program may be configured to adjust the presentation of stimuli and to provide distracting stimuli, in accordance with quantitative evaluations of a person's response, to provide the therapy for visual neglect.

In accordance with yet another aspect of the invention, there is provided a computer-readable storage medium containing a stored program for operating a computer, including instructions for the computer to display, on a selected portion of a display screen, interactive stimuli, to solicit and process responses related to the interactive stimuli, and to quantitatively evaluate the responses relating to the stimuli to indicate a level of success of a person in overcoming visual neglect. The stored program on the storage medium may also include instructions for adjusting a level of difficulty of the solicited responses in accordance with the evaluations, and instructions for controlling the computer to present distracting stimuli in accordance with the evaluations.

It is thus an object of the invention to provide a method and a device for treatment: of visual neglect.

It is another object of the invention that the method and device for treatment of visual neglect be entertaining, in that it is enjoyable for a patient to use.

It is still another object of the invention to provide a method and a device for evaluating a patient's progress in overcoming visual neglect, and to automatically adjust therapy treatments in accordance with this measurement.

The manner in which these and other objects of the invention are achieved will become apparent to those skilled in the art upon review of the drawings and the detailed description of the invention disclosed herein.

BRIEF DESCRIPTION OF THE DRAWINGS

FIG. 1 is a drawing of an inventive computer-based therapy station in use by a person suffering from visual neglect;

FIG. 1A is a drawing of a device that may serve as a storage medium for a program in accordance with the invention, as well as an associated reading device;

FIG. 2 is a first representation of a screen display such as may be displayed on the device of FIG. 1 in accordance with the invention, and also of the associated audio output device shown in FIG. 1;

DETAILED DESCRIPTION OF THE PREFERRED EMBODIMENTS

Figure 3:
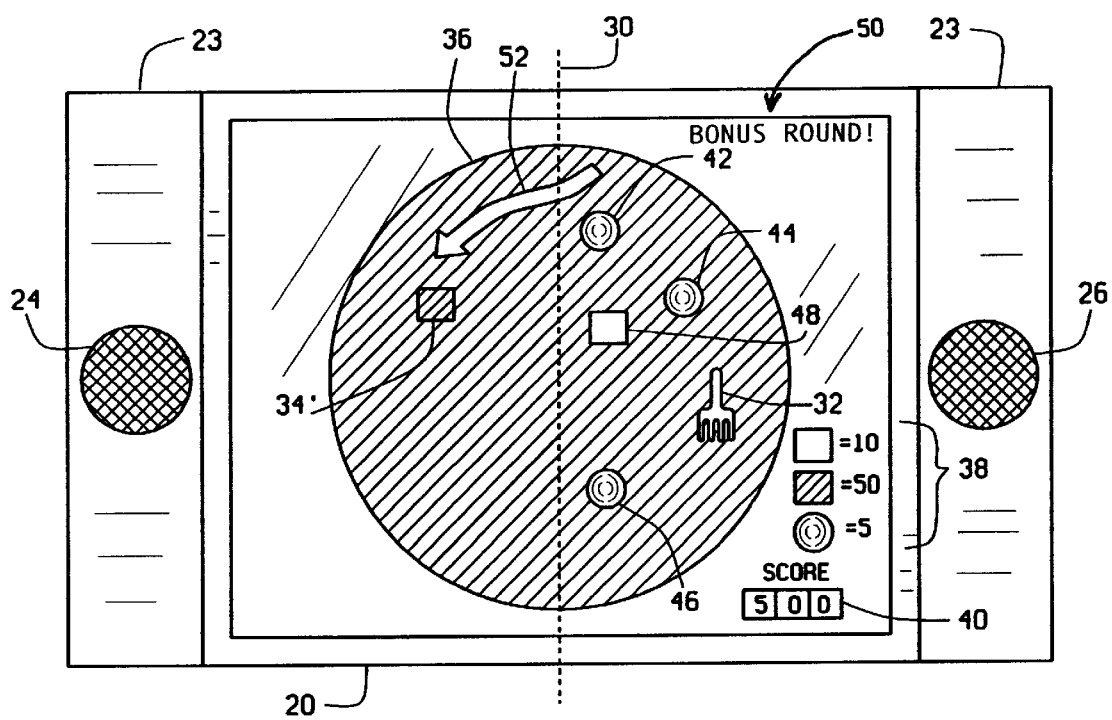
FIG. 3 is a second representation of a screen display such as may be displayed on the device of FIG. 1 in accordance with the invention, and also of the associated audio output device shown in FIG. 1.

FIG. 1 is an illustration of an embodiment of the inventive device 10 of the present invention as it might appear while in use. The illustrated device 10 comprises one or more input devices, here shown as a joystick 14 and a keyboard 22, although it is envisioned that other devices, such as trackballs, touch screens, or a computer mouse may be used either in place of, or in addition to, other input devices. The input device or devices 14, 22 are coupled to a computer system 16 in a suitable way, so that the computer system 16 is responsive to the input device or devices 14, 22. Computer 16 may be a standard, off-the-shelf computer system, such as an IBM® or Apple® computer or compatible system. Alternatively, a special purpose system, such as a video game system, may be used, as it will be recognized that such systems have sufficient computing power to implement the present invention. A monitor 20, preferably with speakers 24, 26 on either side to provide a directional, stereophonic effect, is also provided in this preferred embodiment. As another alternative, a television set (preferably with stereophonic sound) may be substituted for monitor 20, particularly when a video game system is substituted for computer 16. It is to be noted that the individual 12 using the present system for treatment is positioned in front of the monitor 20 so that it is approximately centered in his or her field of view.

Typically, computer 16 will be controlled by an embodiment of a computer program in accordance with the present invention. The computer program may be recorded on any suitable storage device, such as a removable storage device 18A, shown illustratively as a computer floppy disk, which is inserted into a floppy disk drive 18 in computer 16, as is known in the art. However, the computer program may be stored Dn any computer-readable medium, such as a CD-ROM or magnetic tape, for example, or the program may be stored on a hard drive on computer 16 or even permanently stored in a read-only memory. If a video game player is substituted for computer 16, a suitably programmed ROM-based cartridge may be used.

Figure 5:
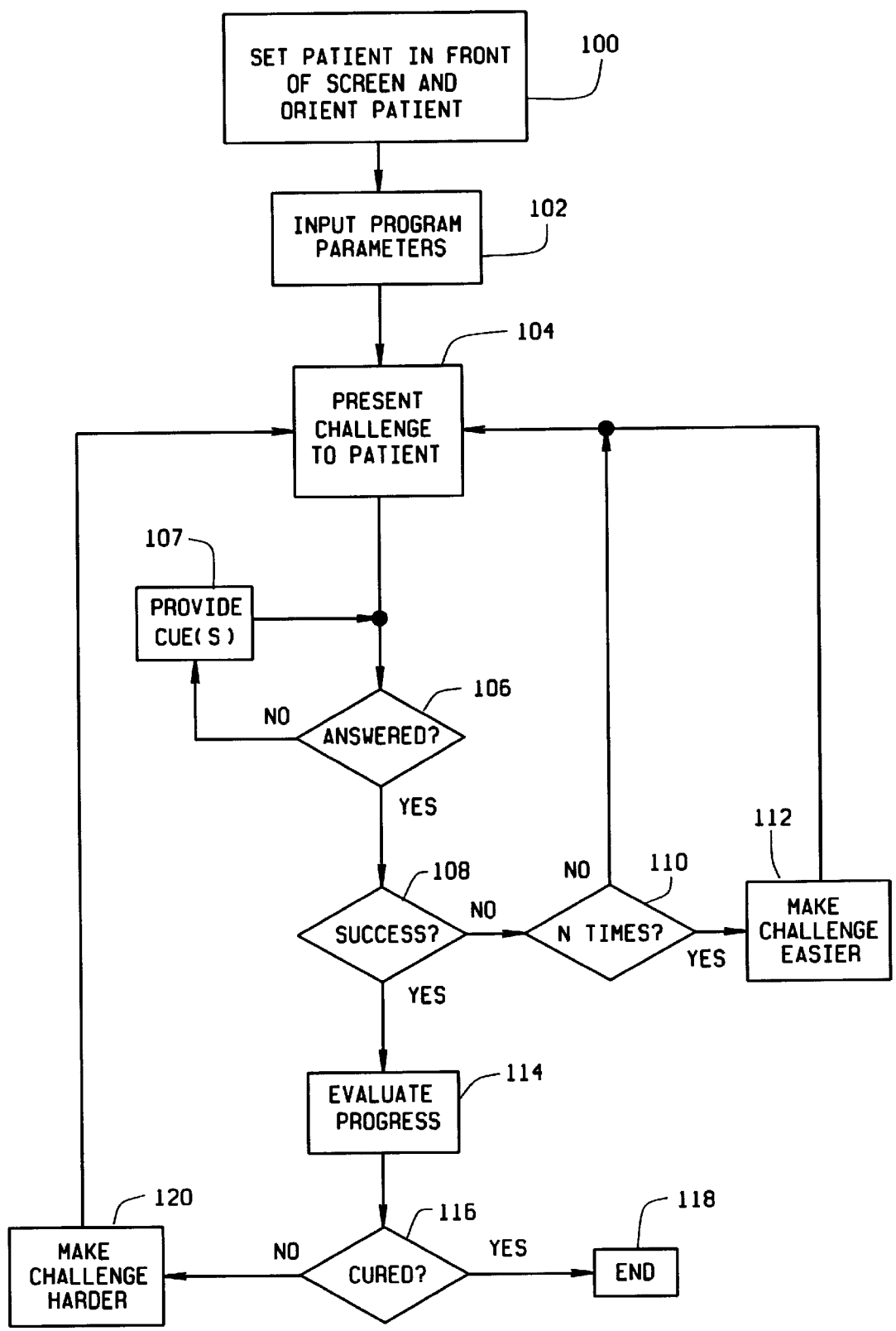
FIG. 5 is a flow chart representing the flow of an embodiment of a computer program in accordance with the present invention.

A high-level flow chart of an embodiment of a computer program in accordance with the invention is shown in FIG. 5. The first step in block 100 need not actually be performed by the computer program, but is shown because it is important that the person receiving the treatment be properly positioned and oriented so that he or she is facing the computer screen. It is very desirable that the person be positioned so that he or she is facing a vertical midline (i.e., an imaginary vertical bisecting line) of the screen. This way, the left and right halves of the screen appear in the left and right portions of the person's field of view, and may be selected to exercise that person's neglected field.

At block 102, program parameters are input. Among these parameters is data indicative of whether the left or the right portion of the field of view is to be exercised. Other parameters, such as a starting level of difficulty of the exercises to be performed, may also be input here. The input may be performed manually, such as by being typed on a keyboard, or previously stored data may be read. Preferably, at the conclusion of each session, or at other times, such as when the program is interrupted, data concerning at least the most recent use of the program is stored, such as to the computer's hard disk. This will allow the program to remember the side of the field of view that is being exercised and to restart in a later session at an appropriate level of difficulty.

At block 104, the computer is instructed to provide a challenge to the patient (i.e., the person receiving the therapy). By "challenge," it is meant that a visual cue on the computer screen or an audible cue via the speakers is presented to the patient, in a manner that addresses the occupational therapy needs of a person afflicted with left or right side visual neglect. Preferably, the patient is subjected to various stimuli via an age-appropriate interactive activity. These activities may include games such as: seek and find objects in space, driving games, airplanes and sports, etc. However, the challenges are designed specifically to address left or right side visual neglect by forcing the patient to look to the left or right in order to play the game or successfully perform the activity. Generally, the activity selected would be one that promotes awareness of the side of the patient that is subject to neglect, and also promote visual scanning, cognitive compensation, and facilitate activation of the afflicted hemisphere of the brain. By addressing these areas, the resulting outcome will be an overall improvement in functional performance for the patient. It may also be desirable for the therapist to provide additional instruction for the patient and his or her family in addition to the computer therapy, with regard to environmental compensation techniques.

An "answer" to the activity, which is input in block 106, corresponds to the input of a suitable response, such as a movement of a joystick or a click of a button at an appropriate time. Block 106 may incorporate a time-out feature that expires if no "answer" is provided by the patient within a predetermined period of time. Execution may also branch to block 107 when no answer is provided within a predetermined period of time, as shown in FIG. 5. At block 107, a cue of some kind, such as an audio and/or visual cue, is provided to the patient in an effort to elicit the desired answer. Execution then branches back to block 106, again to determine whether an answer has been provided. This looping process from block 106 to block 107 and then back to block 106 may be performed a number of times, and the helpfulness of the provided cue (i.e., the extent to which the cue guides the patient to provide the desired answer) can be increased each time execution branches back to block 107, if desired. Where an answer is still not provided by the patient after one or more loops through block 107, or after a predetermined amount of time, this may be deemed an incorrect answer, and execution would move on to block 108.

At block 108, the answer provided (or the lack thereof) is evaluated for correctness. If the answer was correct, the patient's progress in overcoming visual neglect is evaluated at block 114. At some point, the occupational needs of the patient may be deemed met, and the need for therapy would come to an end. This decision would be made at block 116, and the program would terminate at block 118 in that case. More likely, further therapy would be appropriate, and execution would continue at block 120, where parameters controlling the difficulty of the challenge presented in block 104 are adjusted for greater difficulty.

If the challenge presented at block 104 is not determined to be successfully answered at block 108, execution would branch to block 110. If an incorrect answer to the challenge (or no answer) is provided a selected number of times N (for example, 10 times), the challenge may be made easier by adjusting parameters at block 112 before execution resumes at block 104. Otherwise, execution may resume without the parameter adjustment. It is a design choice as to whether the number N is a selectable or an adjustable parameter, or a fixed value that cannot be changed, although care should be taken in the latter case to ensure that the fixed value is not so large as to discourage a patient when the level of difficulty is too high.

It is presumed that the patient or a therapist may interrupt the execution of the program at any time, at which time the program preferably saves any parameters necessary to resume the program at an appropriate level of difficulty at a later time. Although not shown in FIG. 5, it is also preferable that data relating to the progress evaluations and the success of the therapy also be stored for later access, possibly including the printing of a report for evaluation by a therapist.

At a lowest level of difficulty of the challenge presented at block 104, it is expected that only single objects situated at one side of, and adjacent to, the screen's imaginary midline would be presented in the challenge, and that any sound would be presented through only one speaker. As the game or therapy exercise progresses, objects will move from left to right (or vice versa) across the screen and the number of visual (and possibly audio) distractions will increase on both sides of the screen. At the highest level, there will be multiple visual distractions and objects on the screen will reverse direction and move in all directions of movement.

FIG. 2 is an illustration of display 20 in FIG. 1 as it may be viewed by a person 12 as he or she operates the therapy system 10 in accordance with one embodiment of the invention. In this particular embodiment, a game is presented in which an image of a dinner plate 36 is presented. Dinner plate 36 spans the vertical midline 30 of display 20. The nature of the game presented is important to the invention insofar as it should maintain the interest of the person to whom treatment is being rendered, although it is also possible that the game may mimic certain everyday activities or present instructive situations to the afflicted individual. In this case, a moveable cursor 32 in the shape of a fork is provided, and the object of the game is to "clean up" the dinner plate, eating the most tasty food first. The most tasty food is distinguished in this particular embodiment by its shape and color. These rules are reinforced by legend 38 and score indicator 40. In this example, let us assume that it is the patient's left side that is subject to visual neglect. Therefore, in one of the easiest levels of this particular game embodiment, chunks of meat 34, 48 are given higher value than the Brussels sprouts 42, 44, and 46, which serve as distractions. The chunk of meat 34 illustrated on plate 36 under computer control serves as an interactive stimulus at or near the midline 30 (which is an imaginary line that is not actually visible), on a side of the display screen 20 that is subject to neglect. The response solicited by the game (through a visual and/or audio challenge) is to move the fork cursor 32 over to the chunk 34 using a mouse, joystick, or other appropriate means, and collect it with fork cursor 32. Although the score 40 shown to the patient is provided for entertainment, the computer system controlling the screen also quantitatively evaluates the response to the stimuli 34 on the neglected half of screen 20. At lower levels of difficulty, the only interactive stimulus on the screen 20 might be chunk 34 at or near the midline 30. At higher levels of difficulty, other distracting stimuli may be provided, and the chunk 34 may be presented further from the midline 30 of the display, more deeply into the patient's neglected field, to increasingly exercise the person's responses to stimuli on that side.

Speakers 24, 26 shown here on wings 23 attached to display 20, may be provided to present directional auditory stimuli. In some instances, it may be appropriate for the computer to present sounds that apparently emanate from the direction of the interactive stimulus 34. For example, auditory cues such as simulated dinner conversation can apparently emanate from the neglected side (or from any other direction) to direct the patient's attention to the neglected interactive stimulus 34. Such auditory cues may be provided when the expected response is not received by the computer within some predetermined period of time. Alternatively, or additionally, visual cues (such as a hand or finger pointing to food remaining on the plate) can be provided. Preferably, such visual cues are first provided on the unaffected side and may then move towards the affected side and even cross the vertical midline, if desired, to guide the patient's attention back to the side affected by visual neglect.

In the embodiment shown in FIG. 2, a suitable cue may be auditory, such as a voice admonishing the person to finish his dinner. Distracting auditory stimuli may be provided that emanate from other directions, as well, in accordance with a selected level of difficulty. In other embodiments, it may be appropriate to present a single stimulus 34 that moves from a non-neglected side of the screen to a neglected side, across midline 30. Repeated adjustments to the level of difficulty of the exercise may be made, in accordance with the progress of the therapy as measured by the computer.

In addition to, or instead of adding auditory stimuli from speakers, the difficulty of the game may be adjusted by presenting additional distracting visual stimuli 42, 44, 46, 48, or by adjusting properties of the visual stimuli. All of the distracting and helpful stimuli may be provided or withheld in accordance with the then-current level of difficulty provided by the device. The various properties of the stimuli that may be adjusted to provide different levels of difficulty include, but are not limited to, color, size, number of objects comprising the stimulus (i.e., it need not be a single geometric shape, but might comprise a compound object), associated sound direction, geometric complexity, visual contrast, brightness, speed of movement (if the stimuli are presented as moving stimuli) and apparent dimensionality (i.e., whether the objects appear as though they are two- or three-dimensional). The evaluation of the response to interactive stimuli made by the computer system may include either or both:

(a) measuring a number of repetitions of the patient's correct response to a stimulus on a neglected side of the midline of the display screen within a predetermined period of time, and/or (b) measuring a length of time the patient fails to response to a stimulus on a neglected side of the midline of the display screen before a visual or auditory cue is required to focus the attention of the person.

FIG. 3 is a drawing showing a display presented by the same embodiment of the invention represented in FIG. 2, but at a different level of difficulty. In FIG. 3, an additional distraction 50 has been added, and the interactive stimulus 34' on the neglected side of the display 20 has been made smaller. In addition, the contrast between stimulus 34' and plate 36 is reduced as compared to that between stimulus 34 and plate 36 in FIG. 2. Thus, additional cues may be required at some point to direct the patient's attention to stimulus 34', such as a conspicuous arrow 52, or an auditory cue from speakers 24, 26, and preferably one that apparently emanates from the direction of stimulus 34'.

Figure 4:
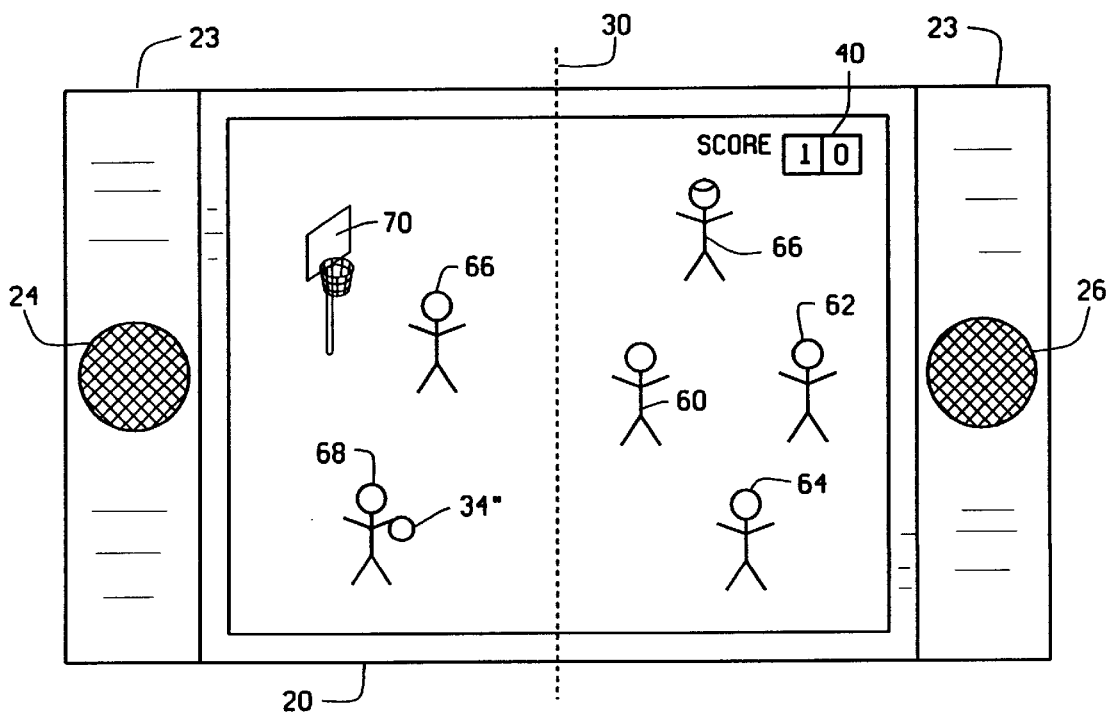
FIG. 4 is a third representation of a screen display such as may be displayed on the device of FIG. 1 in accordance with the invention, and also of the associated audio output device shown in FIG. 1.

FIG. 4 is a representation of a screen display and a game that might be provided in accordance with the invention for a younger patient or a sports fan. In this embodiment, a basketball-like game is provided to the patient. Although the object of the game may appear to the patient to be to grab the ball 34" and shoot a basket 70, in fact, success of the therapy exercises may be measured by the patient using a pointing device to drag a cursor, shown here as a dark-haired player 66, towards the ball 34" on the neglected half of the patient's field of view. Additional distractions (players 68, 66, 60, 62, 64 and score 40) may be provided, depending upon the present level of difficulty needed for the therapy. Speakers 24, 26 may provide either additional distractions, such as crowd noise, or helpful cues, such as an announcer indicating where the ball happens to be. The various parameters that may be varied to control the level of difficulty of the therapy may be adapted to this or other types of games or computer-controlled activities, as apparent to those skilled in the art.

Computer-simulated sports games are among the types of games that are well-suited for therapy involving moving visual stimuli. Stimuli may move across the screen from a non-neglected half of the visual field into the neglected half or vice versa, depending upon the level of difficulty of the exercise, and may change in size as players or objects move across the screen, particularly to simulate a three-dimensional sports game. The rate at which the stimuli move or change size may also be used to advantage. In this preferred embodiment, the screen is effectively divided, from the viewpoint of the computer, via the midline 30 shown in FIGS. 2–4. As should be apparent, however, the imaginary vertical divider may be advantageously moved to the left or right, either further into or away from the side subject to neglect, as necessary or desirable for any specific application of the invention.

It will be apparent to those skilled in the art that many modifications of the above-described exemplary embodiments are possible within the spirit of the invention. Therefore, the scope of the invention should be determined by reference to the claims below and their full range of equivalence under applicable law.

What is claimed is:

1. A method for providing therapy for a patient afflicted with unilateral neglect, the method comprising:
   a) providing a computer-controlled display screen in front of the patient;
   b) displaying, on the display screen under computer control, interactive stimuli to the patient, the interactive stimuli including stimuli on a side of the display screen subject to the patient's neglect;
   c) soliciting responses from the patient including responses related to the stimuli on the side subject to neglect; and
   d) evaluating the responses of the patient to the solicited responses relating to the stimuli on the side subject to neglect to obtain a performance evaluation indicative of a level of success of the patient in overcoming the neglect.

2. The method of claim 1 and further comprising:
   adjusting a level of difficulty presented by the interactive stimuli in accordance with the performance evaluation to increasingly exercise the patient's responses to interactive stimuli on the side subject to neglect.

3. The method of claim 2 and further comprising:
   providing sounds having a same source direction as the stimuli, as observed from a standpoint of the patient.

4. The method of claim 2 wherein the displaying step comprises displaying stimuli situated on a non-neglected side of a vertical midline of the display screen.

5. The method of claim 4 wherein the adjusting step comprises displaying moving stimuli from the non-neglected side to an opposite side of the vertical midline.

6. The method of claim 2 and further comprising providing sounds having a source direction originating from the stimuli, as observed from a standpoint of the patient.

7. The method of claim 2 wherein the adjusting step is repeated a plurality of times, with additional distracting visual stimuli being presented to the patient on the screen, in accordance with the performance evaluations.

8. The method of claim 7 wherein the adjusting step is repeated a plurality of times, with additional distracting sounds other than the sounds having a source direction originating from the stimuli, as observed from a standpoint of the patient.

9. The method of claim 1 wherein the soliciting step includes providing at least one of a visual and an auditory challenge to the patient.

10. The method of claim 9 wherein the evaluating step includes at least one step of a group of steps consisting of:
    measuring a number of repetitions of the patient's correct response to a stimulus on a neglected side of the display screen within a predetermined period of time; and
    measuring a length of time the patient fails to respond to a stimulus on a neglected side of the display screen before a visual or auditory cue is required to focus attention of the patient.

11. The method of claim 9 wherein the soliciting step includes providing at least one of a visual and auditory cue after providing the initial challenge to direct the patient's attention to the stimuli on the side subject to neglect.

12. The method of claim 11 wherein the step of providing one of a visual and auditory cue includes providing a visual cue starting on the non-neglected side and moving in a direction towards the neglected side.

13. The method of claim 10 wherein the stimuli are presented in a video game, responses to the stimuli are provided via at least one member of a group consisting of a mouse, a touch pad, a touch screen, and a joystick, and the adjustment of the level of difficulty includes adjustment of at least one stimulus property selected from a group consisting of color, size, number of objects comprising the stimulus, associated sound direction, geometric complexity, visual contrast, brightness, speed of movement, and apparent dimensionality.

14. A device for providing therapy for a patient afflicted with unilateral neglect, the device comprising:
 a) a display screen;
 b) a computer including a stored program, the computer being coupled to the display screen to operatively display stimuli including stimuli on a side of the display screen subject to the patient's neglect; and
 c) an input device operatively coupled to the computer and configured to receive responses from the patient including responses evoked by the stimuli on the side subject to neglect;
 the computer being configured so that the stored program controls the computer to present the stimuli and to evaluate responses received from the input device, the evaluation being indicative of a level of success of the patient in overcoming visual neglect.

15. The device of claim 14, wherein the stored program is configured to adjust at least one stimulus property selected from a group consisting of color, size, number of objects comprising the stimulus, associated sound direction, geometric complexity, visual contrast, brightness, speed of movement, and apparent dimensionality.

16. The device of claim 15, and further comprising a sound source of adjustable apparent direction, the computer being coupled to the sound source and the stored program being configured to control the computer to produce a sound from the sound source, the sound having an apparent source of origin, from a standpoint of the patient, in a direction of a stimulus appearing on the display screen.

17. The device of claim 15, wherein the stored program is configured to control the computer to adjust the stimulus property in accordance with at least one of:
 (a) a number of repetitions of the patient's correct response to a stimulus on a selected side of the display screen within a predetermined period of time; and
 (b) a length of time before a correct response is received to a stimulus on a selected side of the display screen.

18. The device of claim 17, wherein the stored program is configured to control the computer to present additional distracting stimuli of at least one type selected from the group consisting of visual and auditory distracting stimuli, the stored program also be configured to control the computer to present stimuli and distracting stimuli in accordance with the evaluated responses.

19. The device of claim 18, wherein the stored program is configured control the computer to operate at least one of the display and the sound source to provide cues of at least one type selected from auditory and visual types.

20. A computer readable memory device containing a stored program for operating a computer, including instructions for a computer to display, on a selected portion of a display screen, interactive stimuli; to solicit and process responses related to the interactive stimuli, and to quantitatively evaluate the responses relating to the stimuli, the evaluation being indicative of a level of success of a patient in overcoming visual neglect.

21. The device of claim 20 wherein the stored program includes instructions for a computer to adjust a level of difficulty of the solicited responses in accordance with the evaluation of the responses relating to the stimuli.

22. The device of claim 21 wherein the stored program also includes instructions for controlling the computer to present distracting stimuli in accordance with the evaluation of the responses.

* * * * *